United States Patent
Persaud

(10) Patent No.: US 11,053,454 B2
(45) Date of Patent: Jul. 6, 2021

(54) FRAGRANCE COMPOSITIONS COMPRISING ESSENTIAL OILS AND PRODUCTS COMPRISING SAME FOR PROMOTING WELLNESS

(71) Applicant: THIS WORKS PRODUCTS LIMITED, London (GB)

(72) Inventor: Anna Persaud, London (GB)

(73) Assignee: THIS WORKS PRODUCTS LIMITED, London (GB)

( * ) Notice: Subject to any disclaimer, the term of this patent is extended or adjusted under 35 U.S.C. 154(b) by 0 days.

(21) Appl. No.: 16/593,528

(22) Filed: Oct. 4, 2019

(65) Prior Publication Data

US 2020/0109347 A1   Apr. 9, 2020

(30) Foreign Application Priority Data

Oct. 5, 2018   (GB) ..................... 1816275

(51) Int. Cl.
| | | |
|---|---|---|
| *A61K 8/18* | (2006.01) | |
| *A61Q 13/00* | (2006.01) | |
| *A61K 8/00* | (2006.01) | |
| *C11B 9/00* | (2006.01) | |
| *A61K 8/9789* | (2017.01) | |
| *A61K 8/02* | (2006.01) | |

(52) U.S. Cl.
CPC .......... *C11B 9/0019* (2013.01); *A61K 8/0208* (2013.01); *A61K 8/0212* (2013.01); *A61K 8/9789* (2017.08); *C11B 9/0053* (2013.01)

(58) Field of Classification Search
CPC ....... C11B 9/0019; C11B 9/0053; C11B 9/00; A61K 8/0208; A61K 8/0212; A61K 8/09789; A61K 8/676; A61K 8/922; C11C 5/002; A61Q 19/08; A61Q 13/00
USPC ................................. 512/26, 25, 1
See application file for complete search history.

(56) References Cited

U.S. PATENT DOCUMENTS

| | | | |
|---|---|---|---|
| 10,245,295 B1 | 4/2019 | Smith | |
| 2005/0003976 A1 | 1/2005 | Haze et al. | |
| 2015/0150922 A1* | 6/2015 | Hefti | A61P 25/00 424/733 |
| 2019/0083564 A1* | 3/2019 | Smith | A61K 36/14 |

FOREIGN PATENT DOCUMENTS

CN   105342887 A   2/2016

OTHER PUBLICATIONS

Database GNPD, Mintel; May 11, 2015, anonymous: "Comforting Night Butter", XP055641613, retrieved from www.gnpd.com, Database accession No. 3155759.
Database GNPD, Mintel; Mar. 21, 2016, anonymous: Body Elixir/, XP055641626, retrieved from www.gnpd.com, Database accession No. 3865815.
Database GNPD, Mintel; Jul. 5, 2016, anonymous: "Rose, PAtchouli & Ylang Ylang Natural Wax Candle", XP055641713, retrieved from www.gnpd.com, Database accession No. 4108493.
Database GNPD, Mintel; Aug. 17, 2006, anonymous: "Aromatherapy Candles", XP055641705, retrieved from www.gnpd.com, Database accession No. 576044.
Databse GNPD, Mintel; Jun. 12, 2018, anonymous: "Fruity Scented Purifying Air Spray", XP055641760, retrieved from www.gnpd.com, Database accession No. 5741747.
English translation of CN105342887.
International Search Report issued in co-pending International patent application No. PCT/GB20191052825 dated Nov. 21, 2019.

* cited by examiner

*Primary Examiner* — Jessica Whiteley
(74) *Attorney, Agent, or Firm* — BCF LLP

(57) ABSTRACT

The present technology relates to fragrance compositions comprising essential oils and products comprising the same. The technology also relates to methods of using the fragrance compositions to induce sleep and promote wellness.

12 Claims, 7 Drawing Sheets

Deep calm

Oriental

PEA (control)

Deep Calm vs Oriental [whole group]

Superior temporal gyrus

Deep Calm vs Control [whole group]

Thalamus

Deep Calm [enhanced in women as compared to men]

Gyrus rectus
Putamen
Amygdala

Deep Calm [only women]

Hypothalamus

FRAGRANCE COMPOSITIONS COMPRISING ESSENTIAL OILS AND PRODUCTS COMPRISING SAME FOR PROMOTING WELLNESS

CROSS-REFERENCE TO RELATED APPLICATION

This application claims the benefit of and priority to UK patent application No. 1816275.0, filed on Oct. 5, 2018; the content of all of which is herein incorporated in entirety by reference.

FIELD OF THE TECHNOLOGY

The present technology relates to fragrance compositions comprising essential oils and products comprising the same. The technology also relates to methods of using the fragrance compositions to induce sleep and promote wellness.

BACKGROUND INFORMATION

For a long time, fragranced substances (odors, aromas, scents, perfumes) have been used for mental, psychological, physiological, and even spiritual purposes, to address disorders and aide well-being. Despite this, and the finding that it is the most basic and evocative of our senses (Herz, 2004), olfaction has declined in importance as a sensory modality. Its significance is, however, gradually increasing in both the cosmetic and medicinal industries.

Studies have reported that olfactory stimulation through odor inhalation, application on the skin, massages, or bathes may have psycho-physiological impacts (Haehner, Antje et al 2017; Bower, 2005; Liljenkvist et al, 2010). Interest in this sense is also driven by the search for non-pharmacological approaches to address health issues associated with the stress of the modern life style, such as in disorders of sleep and alertness, and a lack of relaxation.

Olfaction is complex and understanding the mechanism of odor perception is important for achieving an optimal impact of odors on the brain. There is a direct connection from olfactory neurons to the limbic and memory centres of the brain (Gottfried, 2006). The olfactory system may be viewed as an extension of this limbic system, which governs emotions and behaviours (e.g. aggression, fear, mating). Further, it is the only sensory system that connects directly with behavioural centres without the requirement of processing information in other centres, such as the thalamus. Hence a direct behavioural response can be elicited by a particular odorant, which may also be linked to the memory of that odorant.

SUMMARY OF TECHNOLOGY

The present inventors have identified that particular blends of essential oils can achieve positive effects relating to wellbeing in human subjects, particularly individuals suffering from sleep disorders. The inventors have observed that particular brain regions are stimulated in response to the inhalation of particular blends of essential oils thereby supporting the use of these blends to promote health and wellness.

In a first aspect, the present technology provides a fragrance composition comprising: *Boswellia Carterii* oil; *Canaga Odorata*; and *Pogostemon Cablin*.

In certain embodiments, the fragrance composition consists essentially of or consists of essential oils. In certain embodiments, the fragrance composition consists essentially of or consists of *Boswellia Carterii* oil; *Canaga Odorata* and *Pogostemon Cablin*.

In further aspects, the present technology provides products comprising the fragrance compositions according to the first aspect of the technology. Such products include but are not limited to cosmetic products (for example a cream, a lotion, a spray composition, an infused wipe, a face mask, drops, body oil), candles, spray devices.

In further aspects, the present technology provides methods of using the fragrance compositions according to the first aspect of the technology. For example, the technology relates to methods of inducing sleep in a subject by administering fragrance compositions in accordance with the present technology. Further provided are fragrance compositions in accordance with the first aspect of the technology for use in inducing sleep in subjects in need thereof, for example subjects who are sleep-deprived or suffering from a sleep disorder.

The technology also provides method of promoting wellness, reducing fatigue, promoting relaxation, promoting calmness, reducing stress, promoting social confidence, promoting social interaction, promoting empathy, the methods comprising administering to a subject a fragrance composition according to the first aspect of the technology.

The technology further relates to uses of fragrance compositions in accordance with the first aspect of the technology for one or more of inducing sleep in a subject, promoting wellness, reducing fatigue, promoting relaxation, promoting calmness, reducing stress, promoting social confidence, promoting social interaction and promoting empathy.

Other aspects and features of the present disclosure will become apparent to those ordinarily skilled in the art upon review of the following description of specific embodiments.

Figure 1:
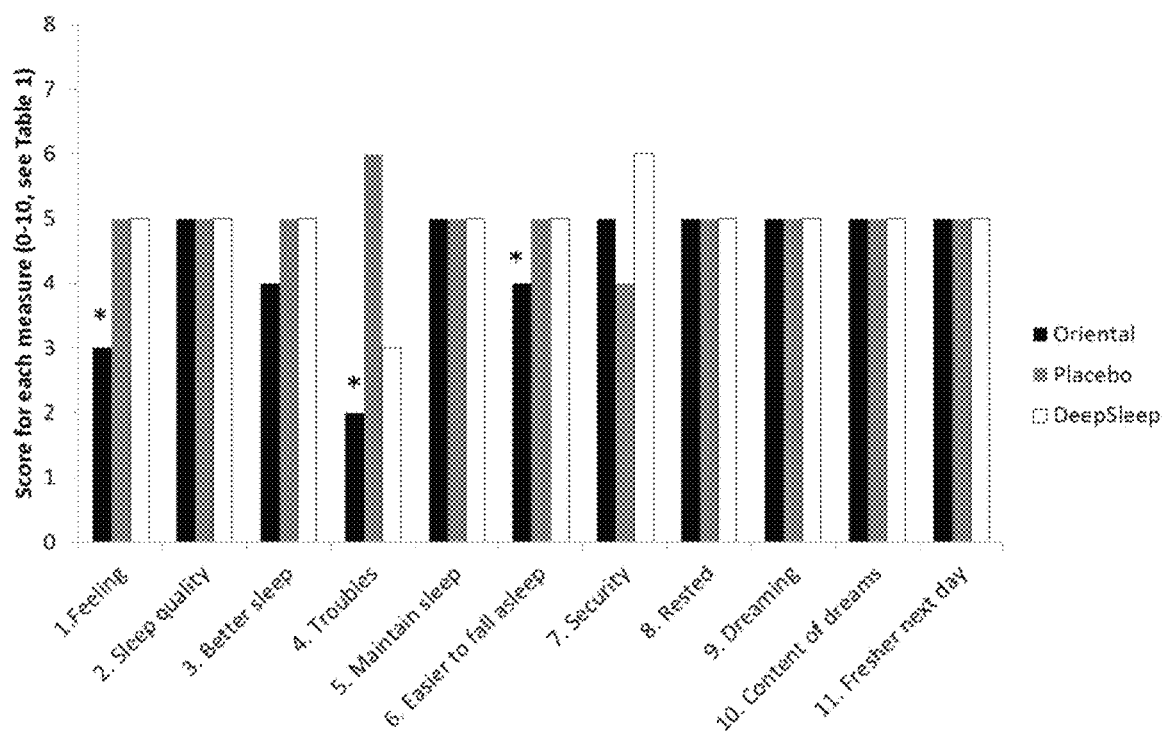
FIG. 1 Results of questionnaire with subjective questions relating to sleep. Completed by subjects administered two test odors—Oriental and DeepSleep—and a placebo. Oriental was rated as significantly better based on measures 1, 4 and 6.

It is to be expressly understood that the description and drawings are only for the purpose of illustrating certain embodiments of the present disclosure and are an aid for understanding. They are not intended to be a definition of the limits of the disclosure and/or of the technology.

DETAILED DESCRIPTION

In a first aspect, the present technology provides fragrance compositions comprising blends of essential oils. The fragrance compositions of the present technology may also be referred to herein as "fragrances", "odors", "odours", "oil-blends". The fragrance compositions are intended for and are suitable for inhalation by human subjects. As described elsewhere herein, the fragrance compositions of the technology find utility in promoting wellness. The fragrance compositions described herein are particularly useful for inducing sleep.

The fragrance compositions of the technology comprise the following essential oil ingredients: (a) *Boswellia Carterii* oil; (b) *Canaga Odorata*; and (c) *Pogostemon Cablin*. The common names for these three ingredients are Olibanum oil, Ylang Ylang and Patchouli. Thus, the fragrance compositions of the technology may, in the alternative, be described as comprising the essential oils: (a) Olibanum oil; (b) Ylang Ylang; and (c) Patchouli. These three oils may be combined so as form a composition of the technology using any suitable technique known to those skilled in the art.

The relative amounts of ingredients (a), (b) and (c) may vary in the fragrance compositions of the technology. In certain embodiments, the ratio of (a) *Boswellia Carterii* oil (Olibanum oil) to (b) *Canaga Odorata* (Ylang Ylang) is from about 1.5:1 to about 2.5:1. In certain embodiments, the ratio of (a) *Boswellia Carterii* oil (Olibanum oil) to (b) *Canaga Odorata* (Ylang Ylang) is 2:1. Alternatively or in addition, the ratio of (b) *Canaga Odorata* (Ylang Ylang) to (c) *Pogostemon Cablin* (Patchouli) is from about 0.5:1 to about 1.5:1. In certain embodiments, the ratio of (b) *Canaga Odorata* (Ylang Ylang) to (c) *Pogostemon Cablin* (Patchouli) is about 1:1. In certain embodiments, the ratio of (a) *Boswellia Carterii* oil (Olibanum oil) to (b) *Canaga Odorata* (Ylang Ylang) to (c) *Pogostemon Cablin* (Patchouli) is about 2:1:1.

The fragrance compositions of the technology may comprise additional ingredients. For example, the compositions may comprise one or more additional essential oils selected from the group consisting of Neroli (*Citrus Aurantium Amara* flower), Mandarin (*Citrus Aurantium Amara* peel), Geranium (*Pelargonium Graveolens* leaf), Chamomile (*Anthemis Nobilis* flower), Sandalwood (*Santalum Austrocaledonicum*), Cedar Atlas (*Cedrus Atlanica*), Ho Wood (*Cinnamomum camphora*), Vetiver (*Vetivera Zizanoides*), Valerian (*Valeriana Officinalis*), Ginger (*Zingiber Officinalis*), Magnolia (*Michelia champaca*) and Jasmine (*Jasminum grandiflorum*—Absolute).

In certain embodiments, the fragrance composition consists essentially of or consists of essential oils.

In certain embodiments, the fragrance composition consists essentially of (a) *Boswellia Carterii* oil (Olibanum oil); (b) *Canaga Odorata* (Ylang Ylang); and (c) *Pogostemon Cablin* (Patchouli). In a preferred embodiment, the fragrance composition consists of (a) *Boswellia Carterii* oil (Olibanum oil); (b) *Canaga Odorata* (Ylang Ylang); and (c) *Pogostemon Cablin* (Patchouli). For embodiments wherein the fragrance composition consists essentially of or consists of (a) *Boswellia Carterii* oil (Olibanum oil); (b) *Canaga Odorata* (Ylang Ylang); and (c) *Pogostemon Cablin* (Patchouli), the compositions may include: (a) about 45-55% *Boswellia Carterii* oil (Olibanum oil); (b) about 20-30% *Canaga Odorata* (Ylang Ylang); and (c) about 20-30% *Pogostemon Cablin* (Patchouli). For embodiments wherein the fragrance composition consists essentially of or consists of (a) *Boswellia Carterii* oil (Olibanum oil); (b) *Canaga Odorata* (Ylang Ylang); and (c) *Pogostemon Cablin* (Patchouli), the compositions may include: (a) about 48-52% *Boswellia Carterii* oil (Olibanum oil); (b) about 23-27% *Canaga Odorata* (Ylang Ylang); and (c) about 23-27% *Pogostemon Cablin* (Patchouli). In a preferred embodiment, the fragrance composition consists of (a) about 50% *Boswellia Carterii* oil (Olibanum oil); (b) about 25% *Canaga Odorata* (Ylang Ylang); and (c) about 25% *Pogostemon Cablin* (Patchouli).

The present technology provides, in further aspects, methods and uses of the fragrance compositions described herein. As reported elsewhere herein, fragrance compositions of the technology can aid sleep thereby benefiting individuals who have difficulties with aspects of sleep including but not limited to quality of sleep, length of sleep, time taken to fall asleep.

In one aspect, the technology provides methods of inducing sleep in a subject, typically a human subject, by administering to the subject a fragrance composition in accordance with the first aspect of the technology. The subject administered the fragrance composition in accordance with the present methods may be a healthy individual without a pre-existing sleep disorder or condition. Alternatively, the subject administered the fragrance composition may be a subject or individual in need of assistance with sleep, for example an individual with a sleep disorder or a sleep-deprived individual. The present technology thus provides a fragrance composition in accordance with the first aspect of the technology for use in inducing sleep in a subject in need thereof. For example, the subject may be an individual who suffers from a sleep disorder, for example acute or chronic insomnia. The present technology thus provides methods of preventing or treating sleep disorders, preferably insomnia, in subjects in need thereof, such methods comprising administering to the subjects a fragrance composition in accordance with the first aspect of the technology. The technology also provides a fragrance composition in accordance with the first aspect of the technology for use in preventing or treating sleep disorders, preferably insomnia, in a subject in need thereof.

Alternatively or in addition, the subject may be an individual suffering from a condition, disease or disorder that impacts on the ability of the subject to experience adequate sleep or good quality sleep. For example, the subject may be a subject suffering from stress or anxiety. Alternatively or in addition, the subject may be suffering from acute or chronic pain. Numerous other conditions, diseases and disorders can impact an individual's sleep patterns and quality of sleep. Individuals with any such conditions, diseases or disorders may be treated in accordance with the methods of the technology.

The term "inducing sleep" is used herein in a broad sense to mean a variety of improvements in quantity or quality of sleep. For example, an inducement of sleep may result in one or more longer periods of sleep. The term is also intended to reflect an inducement of sleep resulting in a period of improved quality sleep, for example a period of more restful, less disturbed sleep. The term may also be interpreted to mean an inducement of sleep resulting in a subject falling asleep within a shorter time period after trying to go to sleep. The differences seen in length of sleep, quality of sleep, time taken to fall asleep will typically be measurable relative to the situation experienced by the subject prior to administration of the fragrance composition.

In addition to effects at the level of sleep, fragrance compositions of the technology have also been shown to activate brain regions associated with wellness, for example regions associated with calmness and relaxation. Thus, the present technology encompasses methods of promoting wellness, wherein the methods comprise administering to a subject a fragrance composition in accordance with the first aspect of the technology. As used herein, the term "wellness" in used a broad sense to mean the general quality or state of the overall body and mind. The fragrance compositions of the present technology have the potential to promote wellness at different levels, for example by reducing fatigue, promoting relaxation, promoting calmness, and/or reducing stress. Thus, in certain embodiments, the present technology provides methods for reducing fatigue, methods for promoting relaxation, methods of promoting calmness, methods of reducing stress, said methods comprising administering a fragrance composition in accordance with the first aspect of the technology. In certain embodiments, the technology provides methods of promoting social confidence, promoting social interaction and/or promoting empathy. As noted above with reference to the sleep-inducing effects of the compositions, all differences will typically be measurable relative to the situation experienced by the subject prior to administration of the composition.

In accordance with the methods of the technology, the fragrance compositions will preferably be administered to subjects via inhalation. Other modes of administration suitable for the delivery of essential oil blends may alternatively be used. Furthermore, as described herein below, the fragrance compositions may be incorporated into cosmetic products, for example sprays or body oils, wherein the route of administration may be affected by the product intended for the end-user.

The technology further provides uses of fragrance compositions in accordance with the first aspect of the technology for inducing sleep in a subject, typically a human subject. Also encompassed by the present technology are uses of fragrance compositions in accordance with the first aspect of the technology for promoting wellness, promoting relaxation, promoting calmness, reducing stress, promoting social confidence, promoting social interaction and/or promoting empathy.

In further aspects, the present technology provides products comprising the fragrance compositions according to the first aspect of the technology. In one aspect, the technology provides cosmetic products comprising a fragrance composition in accordance with any embodiments of the first aspect of the technology. Cosmetic products that may comprise fragrance compositions described herein include but are not limited to creams, lotions, spray compositions, infused wipes, face masks, drops or droplets, body oils.

In certain embodiments, the fragrance compositions may be incorporated into skincare products, for example skincare products intended for topical administration. Such products include but are not limited to creams, lotions, body oils. For embodiments wherein the fragrance compositions are incorporated into products such as creams and lotions, the fragrance composition may be present in an amount from about 0.1 to about 5 wt %.

In certain embodiments, the fragrance compositions may be incorporated into cosmetic products that are formulated as sprays or droplets, for example perfumes and such like. In certain embodiments, the fragrance compositions are spray compositions.

For embodiments wherein the fragrance compositions are incorporated into cosmetic products, the cosmetic products may comprise additional ingredients, particularly standard ingredients used to formulate creams, lotions, perfumes, body oils suitable or intended for application to human skin. In certain embodiments, the products comprise vitamin C.

Further provided herein are products allowing for effective delivery of the fragrance composition to a subject. For example, the fragrance compositions in accordance with the present technology may be incorporated into candles such that the fragrance is released when the candle is burning. Products suitable for delivery of the fragrance compositions further include products capable of delivering the compositions in the form of a spray or droplets. Thus, provided herein is a spray device comprising a spray nozzle in fluid communication with a reservoir, the reservoir containing a fragrance composition according to any of the embodiments described herein and a volatile solvent.

The technology will now be further understood with reference to the following non-limiting examples.

EXAMPLES

A study was carried out to evaluate the influence of different fragrances or odors on the brain. The study was performed to evaluate the behavioural perceptions of odors and changes in the functional magnetic resonance imaging (fMRI) signal. Two odor mixtures—"DeepSleep" and "Oriental" were included in the study alongside a placebo odor. The composition of the "Oriental" odor is shown in Table 1 below.

TABLE 1

| Compositions | | |
|---|---|---|
| Ingredient | Latin name | % |
| Olibanum oil | *Boswellia Carterii* oil | 50 |
| Ylang Ylang | *Canaga Odorata* | 25 |
| Patchouli | *Pogostemon Cablin* | 25 |

The "DeepSleep" odor contained lavender, vetivert, camomile, patchouli and ho wood.

Study Design

Two separate studies (a behavioural study and an fMRI study) were conducted. All subjects gave their written, informed consent, and were remunerated for their participation. The project was approved by the relevant local ethical committees and was conducted in accordance with the Declaration of Helsinki.

A) Behavioural Study

Twelve participants with chronic mild/moderate insomnia (Insomnia Severity Index 17+/−2) entered a double-blind 3-week period home study (in Gothenburg, Sweden) assessing the efficacy of the two odors, "DeepSleep" and "Oriental", compared to a "placebo", which was a synthetic lavender odor. Chronic insomnia was defined as difficulties in falling asleep and/or maintaining sleep for several nights a week (>3 days) for more than 3 months, and having feelings of not being refreshed when waking up in the morning. If the participants were on medication upon entering the study, this was continued throughout the trial period. Otherwise they well as on the Karolinska Sleepiness Scale (KSS, Åkerstedt et al., 1990; 1-very alert, 9 very sleepy). The subjects also filled out a questionnaire (Table 2) about their perceptions.

TABLE 2

| Subjective questions on sleep, after each odor | | |
|---|---|---|
| 1 How did you find your sleep with the odor? | 1 = Convenient | 10 = inconvenient |
| 2 How was your sleep quality with the odor, compared to your typical sleep quality? | 1 = better | 10 = worse |
| 3 Was your insomnia worse or better with the odor? | 1 = better | 10 = worse |
| 4 Did you experience any problems with the odor? | 1 = none | 10 = many |
| 5 How did you find maintaining sleep with the odor? | 1 = easier | 10 = difficult |
| 6 Did you find it easier to get to sleep with the odor? | 1 = much | 10 = not at all |
| 7 Do you feel safer with the odor? | 1 = much | 10 = not at all |
| 8 How do you feel in the morning when you wake up? | 1 = more rested | 10 = more tired |
| 9 Did you experience dreams with the odor, as compared to your typical sleep? | 1 = much more | 10 = much less |
| 10 What was the content of your dreams like? | 1 = pleasant | 10 = unpleasant |
| 11 After waking up with the odor, how did you experience daytime? | 1 = drowsy | 10 = alert |
| 12 After waking up with the odor, did you experience any troubles? | 1 = No difficulty 2 = Headache, 3 = Darkness, 4 = Dizziness, 5 = Nausea, 6 = Fatigue, 7 = Other | |
| 13 Did you feel that the odor effect decreased after . . . ? | 1 = One day, 2 = 2dgr, 3 = 3 dgr, 4 = Not at all throughout the test period, 5 = No effect from the beginning | |
| 14 At the end of the test: Do you prefer sleep with . . . ? | 1 = $1^{st}$ odor, 2 = $2^{nd}$ odor, 3 = 3rd odor, 4 = No odor | | had to be healthy. The exclusion criteria were presence of illnesses or newly discovered problems (<6 months), for example, sleep apnea, untreated metabolic disorders or high blood pressure. The participants should not have changed any medication in the prior 4 weeks to commencing the study. Participants were selected by advertising at the sleep clinics and through leaflets on boards.

Odors were randomly assigned in a counter-balanced order. Subjects slept the first 3 nights as usual, and for the proceeding 4 nights. They sprayed the first randomized odor on their pillowcase before bedtime, evaluating their experiences at the end of the period. Following a few "washing" nights (new pillowcase) without an odor, they slept 4 nights with a second odor, and the same procedure continued with the third odor.

The experimental measures included objective (physiological) and subjective (self-report) elements. Physiological movement data were collected using wrist actigraphy (Actiwatch; Cambridge Neurotechnology Ltd, Cambridge, UK). The actigraphy watch consisted of an accelerometer that was worn continuously during the study and these data were stored in the unit. The data were analyzed using validated algorithms for the recognition of basic sleep-wake patterns and frequencies of movements. Each subject filled in a sleep diary, which included a report of the participants' bed time and waking-up time, which defined their period of sleep and was used for the analysis of actigraphy data. The actigraphy analyses were conducted on this sleep period, with output variables including sleep latency, assumed sleep, total wake time, sleep fragmentation index, number of bouts of immobile time and their frequency, and the number of sleep bouts and their duration.

For the subjective reports, subjects filled out the daily sleep diary, which also included reports on their daytime behaviour and sleep perception, with free comments about their night's sleep. They were also able to note if there were any environmental changes of importance. On awakening, they noted their 'sleep quality' on a visual analog scale (VAS; with the end-anchors 'Very good' and 'Very bad'), as The odors were coded so that the analysis was conducted blind. The data were analyzed in Prism (version 7; GraphPad, San Diego, Calif.), where the data were tested for normality. Parametric statistics were used to analyze the actigraphy, KSS, and sleep quality measures, and non-parametric statistics to analyze the questionnaire data. Significant differences were sought at $P<0.05$ and multiple comparison corrections were applied.

B) fMRI Study

Participants:

Thirty participants were tested –15 men and 15 women, aged 20-35 (mean 24.4 SD+/−3.2 years). All of them exhibited normal olfactory function regarding threshold, discrimination and identification as controlled with the Sniffing Sticks test (Burghardt, Germany)

Method:

The fMRI measurement of the blood oxygenation level dependent (BOLD) signal was performed with a 3 Tesla scanner (Sonata; Siemens, Erlangen, Germany). Three odors were presented singly to both nostrils during scanning. The odors were "DeepSleep", "Oriental" and a placebo (Phenylethylalcohol [PEA]).

In order to ensure a subjective iso-intense odor perception, a pre-test with various dilutions per odor was conducted in a sample of 15 different participants. Each of the odors was presented three times in a randomized order and the participants rated the odorants' intensity. The averaged ratings per odor were compared to each other with a t-test and semi-intense odor dilutions were chosen for the fMRI presentation. Based on the pre-test results, a dilution of 6.25% (made in 1,2-propanediol) was chosen for DeepSleep and Oriental and a dilution of 100% for the control odor in order to achieve semi-intense perception.

Procedure:

Six runs of odor presentation in on-off (inspiration/exhalation) blocks were performed in a randomized order. The exact number of presentations of a single odor per run depended on the subject's own breathing frequency, but this was ~10 presentations. Each of the odors was hence presented in two runs, in order to enhance statistical power. During each on block the odor was presented continuously for 10 seconds, followed by a baseline of at least 17 seconds during which clean air was presented. The odors, as well as the clear air, were applied by a computer-controlled olfactometer with respiratory feedback that enabled synchronization between in-breathing and odor presentation. The tubes containing the odors were positioned directly in the scanner and were connected to the participant's nose via a 2 mm tube of 1 m length, which enabled direct and fast stimulus presentation. The constant airflow was set to 2 l/min.

After each run, the participants were asked to verbally rate the intensity of the odor on a scale from 0 (not intense at all) to 5 (very intense). A total of 150 volumes per run were acquired by means of a 38 axial-slice matrix (TR: 3000 ms/TE: 40 ms, FA 90; matrix=348*348). Following the fMRI sessions, a T1-weighted image was acquired in the sagittal direction by using a T1-MPR sequence (TR: 1890 ms/TE: 3.24 ms; matrix=238*348): This scan was run to allow individualized brain normalization in the later statistical analysis.

Statistical Analysis:

Intensity ratings were analyzed using SPSS 22 (IBM, Armonk, N.Y.). The main effect of odor quality and repetition, as well as the interaction effect, were tested in a repeated measures ANOVA. Post hoc tests were computed as t-tests for dependent measurements and were Bonferroni-corrected for multiple comparisons. Neural data analyses was performed with SPM 12 software (Statistical Parametric Mapping; Wellcome Department of Imaging Neuroscience, Institute of Neurology at University College London (UCL), UK), implemented in Matlab R2015b (Math Works Inc, Natick, Mass.), following spatial pre-processing with the same software (spatial filtering: high pass filter=128 Hz, registering, realignment, co-registration between functional and structural images, normalization using segmentation procedure, smoothing by means of 6×6×6 mm3 FWHM Gaussian kernel). SPM matrices reflecting the ON-OFF differences were calculated for each session, based on the general linear modeling approach. As the odors were not perceived as semi-intense (as per the pre-test) in the scanner, all activations were corrected for the individual intensity rating. Analyses were based on t-tests with global height threshold p<0.001 for the overall olfactory activation. All activation coordinates are presented in MNI space (Montreal Neurological Institute).

Connectivity Analysis:

The pre-processed data were analyzed with the connectivity toolbox in SPM. The primary olfactory cortex (piriform cortex) was used as a seed and the connectivity from this very first olfactory target area to other areas in the brain was modeled. A statistical threshold of 0.05, FDR corrected, was used.

Results

A) Behavioural Study

Reliable actigraphy measures were obtained from n=8 subjects (6 women and 2 men). With "DeepSleep" there was less activity during sleep than with Placebo (mean difference=−6563, p <0.001) and "Oriental" (mean difference=9556, p=0.030). With the placebo there was a decrease in the number of immobile phases (5.57; t=3.78, df=7, p=0.007) and more wake time (%) than "DeepSleep" (mean difference=158.8, p=0.046).

Reduced alertness was found in the KSS, comparing the baseline sleep to sleep with the DeepSleep odor (mean difference=1.62, P=0.029). In 50% of subjects, the impact of the odor lasted 1-2 days. There was no clear preference for a particular odor, but 80% preferred sleeping with an odor, rather than no odor. None of the odors affected the subjects' dreams. Occasional headaches and dry mouths were reported.

The results of the subjective assessment questionnaire are shown in FIG. 1.

B) fMRI Study

1) Perception of the Odors within the Scanner

Figure 2:
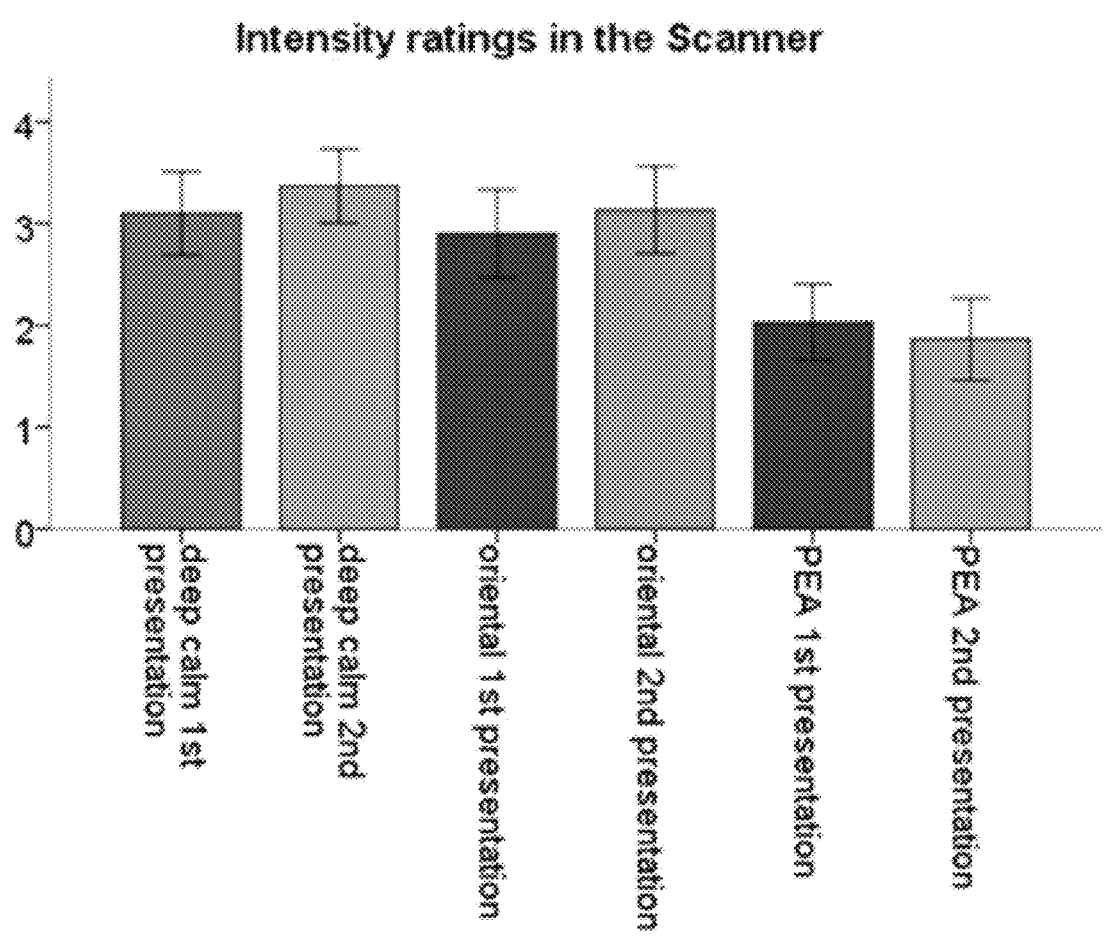
FIG. 2 Intensity ratings of odors within the scanner. Significant effects of the odors were observed but no effect of odor repetition. The error bars indicate the 95% confidence interval.

There was a significant effect of odor quality on intensity ratings (F[2,29]=29,3, p<0.001), but no effect of repeated presentation (F[1,30]=1,6, p=0.21), and no significant interaction effect ([2,29]=1,6, p=0.20, FIG. 1). Post hoc test revealed that both of the odors, DeepSleep and Oriental, were rated as significantly more intense than the control odor of PEA. See FIG. 2.

2) Overall Neural Activation

Figure 3:
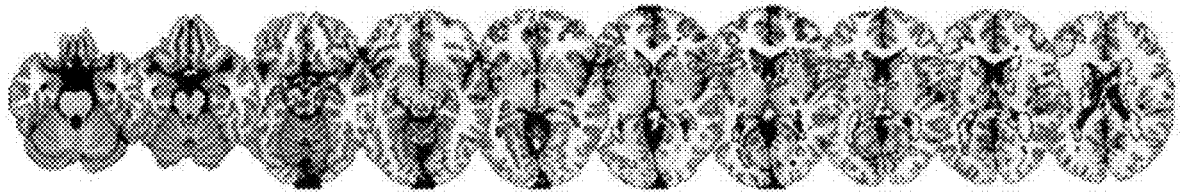
FIG. 3 Comparison of the neural activation following exposure to the DeepSleep, Oriental and Control (PEA) odors. The activations vs baseline are adjusted for intensity effects and presented on a standardized template with a height threshold of $p<0.001$, uncorrected.
Figure 3:
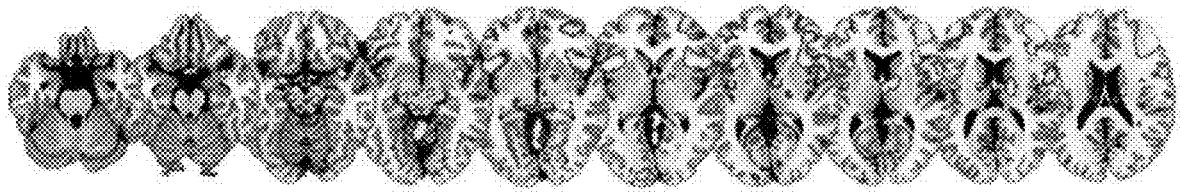
Figure 3:
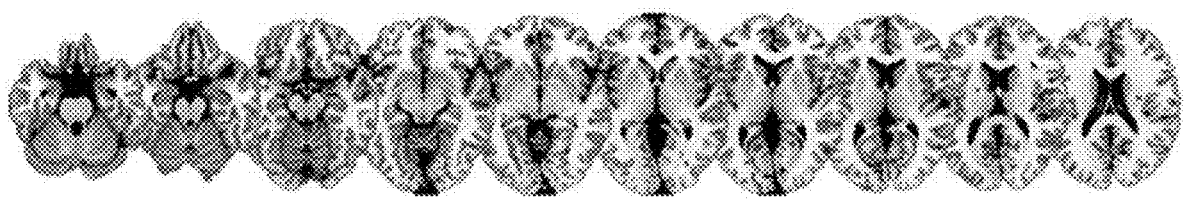

The presentation of the odors was related to a clear activation of olfactory relevant areas, such as the orbitofrontal cortex, amygdala and insula (see FIG. 3). Note that the middle cingulate cortex was responsive as well—suggesting that the odors evoked hedonic responses. Furthermore, there were neural response patterns in the hLP1 region which suggests a trigeminal perception in all of the odors.

3) DeepSleep

Figure 4:
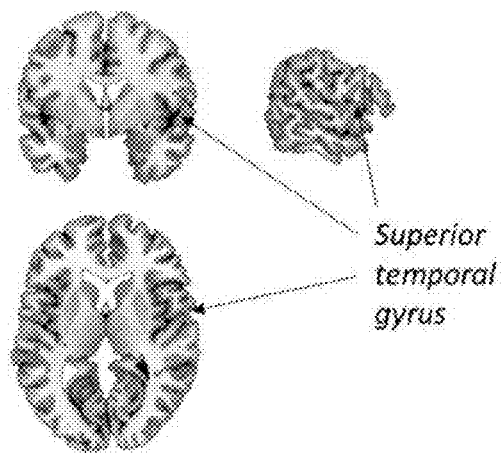
FIG. 4 Neural activation following the inhalation of the DeepSleep odor, adjusted for intensity effects, and presented on a standardized template. The threshold level is set to $p<0.01$, for visualization purpose.
Figure 4:
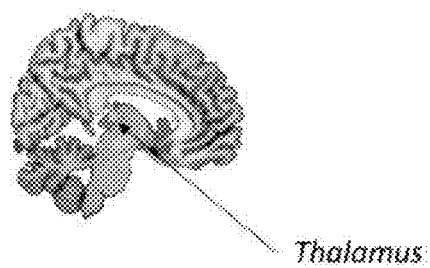
Figure 4:
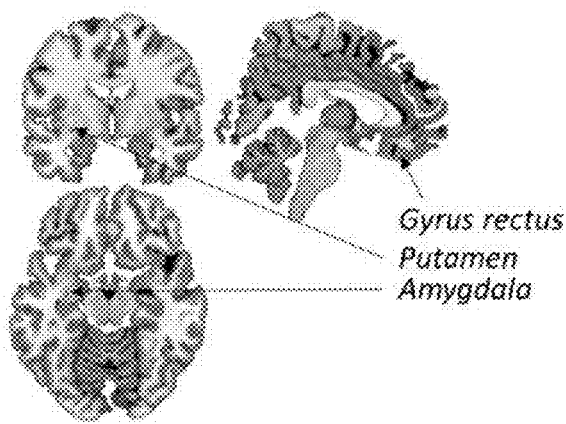
Figure 4:
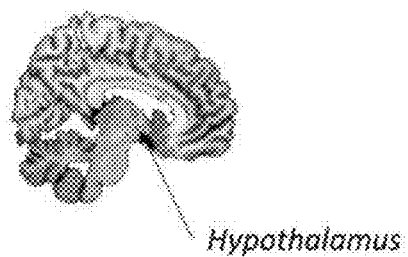

The results are shown in FIG. 4.

DeepSleep vs Control: After the correction for differences in intensity ratings, the DeepSleep odor was related to higher BOLD signal change in the thalamus and middle frontal gyrus. None of the primary or secondary olfactory projection areas and none of the trigeminal projection areas proved to be significantly enhanced for DeepSleep, as compared to the control odor.

DeepSleep vs Oriental: After the correction for differences in intensity ratings, the DeepSleep odor was related to a higher BOLD signal change in the right superior temporal gyrus.

Looking for a possible oxytocin release, it was specifically checked whether the odors would be related to enhanced hypothalamic activation. For this purpose a ROI sphere of 6 mm (around 3 0-8; MNI space) was created and a liberal threshold of p<0.01 was applied.

For DeepSleep, this region proved to be activated with very low effect size in women [T=2.5, p=0.007, k=1], but not in men. Furthermore, the activation was significantly higher in women as compared to men [T=2.7, p=0.004, k=4].

4) Oriental

Figure 5:
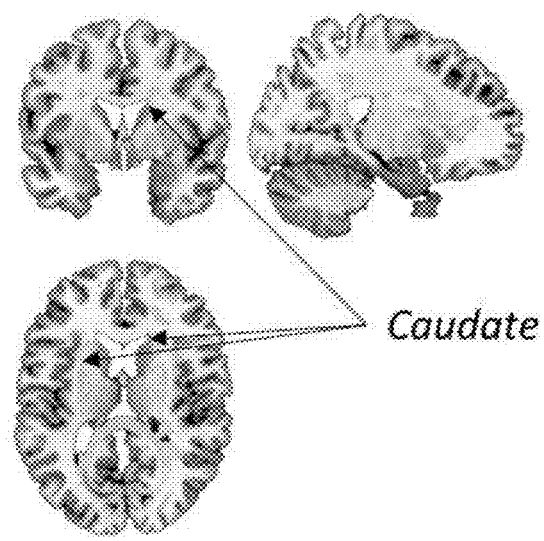
FIG. 5 Neural activation following the inhalation of the Oriental odor, adjusted for intensity effects, and presented on a standardized template. The threshold level is set to $p<0.01$, for visualization purpose.

The results are shown in FIG. 5.

Oriental vs Control: After the correction for differences in intensity ratings, the Oriental odor was related to enhanced BOLD signal changes in the right and left caudate, and a cluster which bordered the right thalamus. None of the primary or secondary olfactory projection areas and none of the trigeminal projection areas proved to be significantly enhanced for Oriental, as compared to the control odor.

Oriental vs DeepSleep: There was no enhanced activation in Oriental odor as compared to the DeepSleep odor.

Focus on hypothalamic activation: It was specifically checked, whether the odors would be related to enhanced hypothalamic activation. For that respect a ROI sphere of 6 mm [around 3 0-8; MNI space] was created and a liberal threshold of p<0.01 was applied. For Oriental, there was a slight activation in men [T=2.6, p=0.005, k=2], but not in women. However, the gender differences were not significant.

Connectivity Analysis

Figure 6:
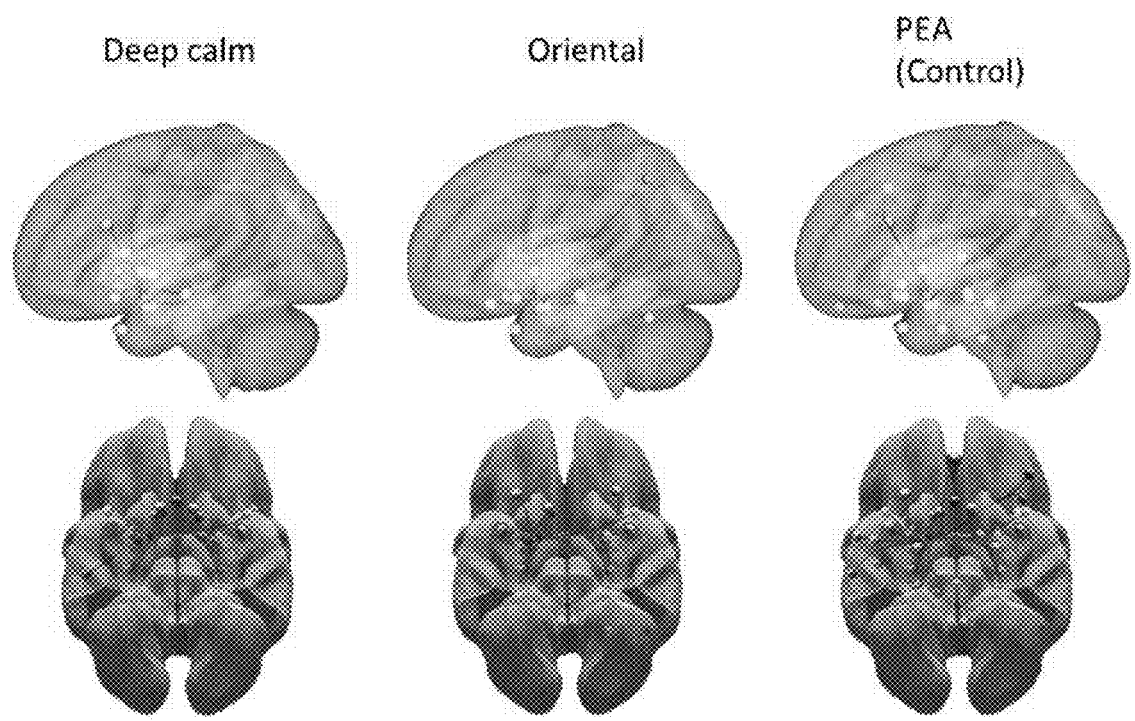
FIG. 6 Results of connectivity studies. The averaged connectivity of all of the subjects is displayed. Positive connectivity is indicated by red lines, negative by blue lines. All results are presented at a threshold of 0.05, FDR-corrected for multiple comparisons.

The results are shown in FIG. 6.

With each of the odors, the piriform cortex was significantly positively connected to other olfactory relevant and emotionally relevant brain areas, such as the hippocampus, anterior insula, amygdala. The overall connectivity was most wide spread and strongest in the control odor (PEA: intensity: 170; 41 nodes, deep calm: intensity 102; 23 nodes, oriental: intensity: 86, 18 nodes).

With DeepSleep, there was a negative connectivity between the piriform cortex and the superior temporal cortex. With Oriental there was a negative connectivity between the piriform cortex and the posterior cingulate cortex (a node of the default mode network). In the control odor, negative connectivity was detected to the left parietal frontal gyrus (the frontal executive control network).

Differences Between the Odors

Figure 7:
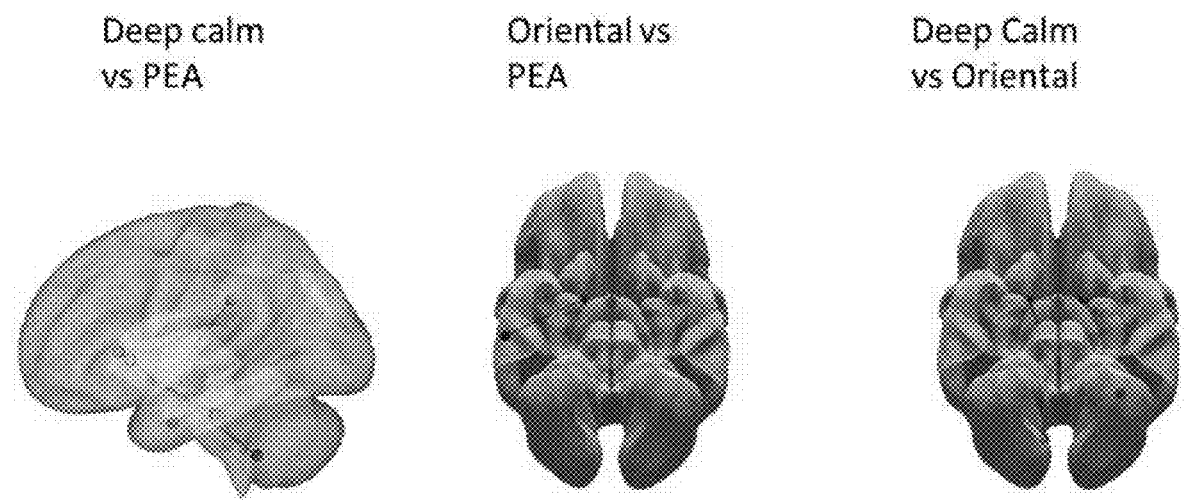
FIG. 7 Connectivity results showing differences between the odors. The averaged connectivity of all of the participants is displayed. Positive connectivity is indicated by red lines, negative by blue lines. All results are presented at a threshold of 0.05, not corrected for multiple comparisons.

Differences of connectivity were calculated between the odors. There were general differences in intensity and number of nodes but for none of the specific connections were found a significant effect in the group comparison. See Table 3 below and FIG. 7.

All odors showed the expected activations in olfactory areas with significant differences between DeepSleep, Oriental, and PEA. DeepSleep was related to the highest neural central activation in very important areas of the brain. Oriental in turn was more effective than PEA, impacting more brain areas than PEA.

There was no effect of repeated exposure to the odor. Each odor was presented twice and presentations were interrupted by presentation of a different odor (e.g. DeepSleep-Oriental-PEA followed by a block DeepSleep-PEA-Oriental etc). There were no significant differences in neural activation between both presentations of the same odor. As there was no effect of repeated stimulation, it appears that the neural effect does not weaken over time—at least if the stimulation is interrupted by the presentation of different odors. However, olfaction is also known for rapid adaptation. This means that an odor which is presented uninterrupted for a long time, will not be perceived anymore. For this reason, a block design with rather short blocks was chosen.

Activation of the middle cingulate cortex, which was especially seen in DeepSleep suggested that the odors evoked hedonic responses, although multiple areas are involved in hedonic coding. Activation of the caudate (Oriental) and the putamen (DeepSleep) areas suggest the activation of reward processes, since both these dopaminergic structures form one of the major brain complex composing the reward system.

The observed hippocampal involvement—more pronounced in women—may be related to processes of memory. The speculative question is whether the odor is more familiar to women or that women try harder to relate a memory to the odor.

The overall connectivity in this study was stronger and more widespread for the control odor. Oriental and PEA (but not DeepSleep) cause a negative connectivity to the posterior cingulate cortex, which is a part of the default mode network suggesting that these odors seem to prepare the brain to react.

TABLE 3

Differences of connectivity

| | Reduced connectivity | Enhanced connectivity |
|---|---|---|
| Oriental vs PEA | right superior temporal gyrus (p(uncorr) = 0.011) | |
| DeepSleep vs PEA | right superior temporal gyrus, posterior division (p(uncorr) = 0.001) right superior temporal gyrus, anterior division (p(uncorr) = 0.046) right inferior temporal gyrus (p(uncorr) = 0.001) left inferior temporal gyrus (p(uncorr) = 0.001) right parahippocampal gyrus (p(uncorr) = 0.038) right hippocampus (p(uncorr) = 0.041) posterior cingulate gyrus (p(uncorr) = 0.029) | left frontal operculum - a division of the salience network (p(uncorr) = 0.001) left anterior insula, which is a division of the salience network (p(uncorr) = 0.007) |
| DeepSleep vs Oriental | posterior cingulate gyrus (p(uncorr) = 0.023) right cuneal corex (occipital lobe) (p(uncorr) = 0.025) right cuneal corex (occipital lobe) (p(uncorr) = 0.025) left fusiform corex (occipital lobe) (p(uncorr) = 0.039) | Left pirifom cortex |

Discussion

The findings of the study on subjects with insomnia showed the behavioural impact of the odors, with differing results for each odor. Interesting is that this effect decreased after few days. The subjective evaluation rated "Oriental" significantly better than "DeepSleep" although actigraphy indicated that subjects spent less time awake with "DeepSleep". In the fMRI study, odors were embedded in a constant flow of air directly delivered to the nostrils hence avoiding any sudden mechanical stimulation. It was hypothesized that the odors would have an impact on well-being and sleep. The neural activation showed a pronounced effect of the odors on the olfactory system and a coupling between the primary olfactory region and other brain areas. The anterior intra-parietal sulcus (an area involved in somatosensory integration) was involved due to stimulation of the trigeminal nerve.

The odors in this study activated specific brain areas related to reward processing for the Oriental odor and socio-emotional processing for Deepsleep. The results suggest that different odor mixtures may relate to specific behavioural alterations. Taking the findings together (hedonic and social brain areas as well as hypothalamus response) we believe that the odors may evoke a feeling of social comfort, trust and calmness.

The present technology is not to be limited in scope by the specific embodiments described herein. Indeed, various modifications of the technology in addition to those described herein will become apparent to those skilled in the art from the foregoing description and accompanying figures. Such modifications are intended to fall within the scope of the appended claims. Moreover, all aspects and embodiments of the technology described herein are considered to be broadly applicable and combinable with any and all other consistent embodiments, including those taken from other aspects of the technology (including in isolation) as appropriate.

Various publications and patent applications are cited herein, the disclosures of which are incorporated by reference in their entireties.

The invention claimed is:

1. A fragrance composition consisting of:
   (a) *Boswellia Carterii* oil;
   (b) *Canaga Odorata*; and
   (c) *Pogostemon Cablin*.

2. The fragrance composition according to claim 1, wherein the ratio of (a) to (b) is from 1.5:1 to 2.5:1 and/or the ratio of (b) to (c) is from 0.5:1 to 1.5:1.

3. The fragrance composition according to claim 2, wherein the ratio of (a) to (b) is about 2:1 and/or wherein the ratio of (b) to (c) is about 1:1.

4. The fragrance composition according to claim 1, consisting of:
   (a) about 50% *Boswellia Carterii* oil;
   (b) about 25% *Canaga Odorata*; and
   (c) about 25% *Pogostemon Cablin*.

5. A method of inducing sleep in a subject, the method comprising administering to the subject a fragrance composition according to claim 1.

6. A method of promoting wellness, reducing fatigue, promoting relaxation, promoting calmness, reducing stress, promoting social confidence, promoting social interaction or promoting empathy, the method comprising administering to a subject a fragrance composition according to claim 1.

7. A cosmetic product comprising the fragrance composition according to claim 1.

8. The cosmetic product according to claim 7, wherein the product is a cream, a lotion, a spray composition, an infused wipe, a face mask, drops, body oil.

9. The cosmetic product according to claim 7, wherein the product further comprises vitamin C.

10. The cosmetic product according to claim 7, wherein the product is a cream and comprises the fragrance in an amount of from 0.1 to 5 wt %.

11. A candle comprising the fragrance composition according to claim 1.

12. A spray device comprising a spray nozzle in fluid communication with a reservoir, the reservoir containing the fragrance of claim 1 and a volatile solvent.

* * * * *